(12) United States Patent
Schnitzler

(10) Patent No.: US 8,172,838 B2
(45) Date of Patent: May 8, 2012

(54) FOUR-POSITION ROCKER SWITCH FOR ELECTROSURGICAL HANDPIECE

(75) Inventor: Uwe Schnitzler, Tübingen (DE)

(73) Assignee: Erbe Elektromedizin GmbH, Tübingen (DE)

(*) Notice: Subject to any disclaimer, the term of this patent is extended or adjusted under 35 U.S.C. 154(b) by 1205 days.

(21) Appl. No.: 11/920,706

(22) PCT Filed: May 17, 2006

(86) PCT No.: PCT/EP2006/004688
§ 371 (c)(1),
(2), (4) Date: Nov. 19, 2007

(87) PCT Pub. No.: WO2006/125558
PCT Pub. Date: Nov. 30, 2006

(65) Prior Publication Data
US 2009/0076504 A1 Mar. 19, 2009

(30) Foreign Application Priority Data
May 25, 2005 (DE) .......................... 10 2005 024 221

(51) Int. Cl.
*A61B 18/00* (2006.01)
(52) U.S. Cl. ........................................... 606/45; 606/41
(58) Field of Classification Search ................ 606/41–45
See application file for complete search history.

(56) References Cited

U.S. PATENT DOCUMENTS

| | | | |
|---|---|---|---|
| 4,112,950 A | | 9/1978 | Pike |
| 4,655,215 A | * | 4/1987 | Pike ................................ 606/42 |
| 4,658,815 A | | 4/1987 | Farin et al. |
| 4,931,047 A | * | 6/1990 | Broadwin et al. ............... 604/22 |
| 5,234,427 A | * | 8/1993 | Ohtomo et al. .................. 606/37 |
| 6,528,741 B2 | * | 3/2003 | Walker .......................... 200/5 R |
| 2002/0058938 A1 | * | 5/2002 | Cosmescu ...................... 606/45 |

FOREIGN PATENT DOCUMENTS

| | | |
|---|---|---|
| DE | 689 21 716 | 7/1995 |
| DE | 195 03 702 | 8/1996 |
| DE | 690 25 849 | 9/1996 |
| EP | 0 310 431 | 4/1989 |
| EP | 0 423 757 | 4/1991 |
| EP | 1 201 196 | 5/2002 |
| EP | 1 214 913 | 6/2002 |
| EP | 1 293 171 | 3/2003 |
| FR | 2 368 790 | 5/1978 |
| JP | 7-41044 | 5/1995 |
| JP | 2001-029353 | 2/2001 |
| JP | 2002-330977 | 11/2002 |

OTHER PUBLICATIONS

English machine translation of FR 2368790.*
German Examination Report for DE 10 2005 024 221.9-35.

* cited by examiner

*Primary Examiner* — Linda Dvorak
*Assistant Examiner* — Amanda Scott
(74) *Attorney, Agent, or Firm* — Dickstein Shapiro LLP

(57) ABSTRACT

A surgical apparatus includes an actuation unit disposed on a handle and a control unit providing at least three modes for controlling the electrical instrument. The actuation unit contains a switching rocker with an operating element, which is rotatable about a rocker axis that can be shifted perpendicular to the surface of the handle, so that starting from an initial position a first or second function position can be reached by forwards or backwards rotation about the rocker axis, and a third function position can be reached by pressing the operating element inward, two sensors being disposed on the operating element, one on the left and the other on the right side of the rocker axis, in such a way that by means of the sensors the function position selected by means of the switching rocker can be determined by the control unit.

11 Claims, 4 Drawing Sheets

FOUR-POSITION ROCKER SWITCH FOR ELECTROSURGICAL HANDPIECE

FIELD OF THE INVENTION

The invention relates to a surgical device, and specifically to an electrosurgical device with a four-position rocker switch.

BACKGROUND OF THE INVENTION

In modern surgery a large number of electronic components and electrical devices are employed to ensure that operations are performed reliably and without harm to the patient. For instance, high-frequency surgery has been used for years, in both human and veterinary medicine, in order to coagulate and/or to cut biological tissue. In this procedure high-frequency current is conducted through the tissue that is to be treated or removed, so that owing to protein coagulation and dehydration the tissue is altered or disintegrates. The tissue thus contracts in such a way that the vessels are closed and bleeding is stanched. A subsequent increase in current density causes an explosive vaporization of the tissue fluid and the cell membranes are torn apart, so that the tissue is completely transected. Methods of this kind, as opposed to a purely mechanical cutting procedure, offer the advantage of haemostasis at the cut edges.

In principle both the coagulation and the cutting can be performed with the same medical instrument. In both modes of operation the instrument is supplied with high-frequency voltage from a high-frequency generator. To control the high-frequency generator a large number of parameters are required, and these must be chosen according to which of the two operation modes is intended, the nature of the tissue and other criteria in order to achieve an optimal result of the coagulation or cutting. Modern instruments provide a large number of modes that assemble the parameters needed for a particular application scenario. In practice it has turned out that during an operation a frequent alternation between a particular coagulation mode and a particular cutting mode is necessary, whereas it is less common for a change to be made between different cutting modes or different coagulation modes as such. To satisfy the latter requirement as well, the applicant provides instruments for coagulating and cutting biological tissue which are constructed so that two buttons on the handle of the instruments can be used to switch directly between a preset coagulation mode and a preset cutting mode, while a third button on the handle enables suitable modes to be selected for the first and the second button. A disadvantage of this three-button handle resides in the fact that in order to operate the buttons reliably, the handle must be securely gripped. Furthermore, it requires considerable time for a user to become accustomed to "blind" operation of the three keys, because of the need to change continually between different finger positions. It can also happen that due to the actuation of the wrong button, or several buttons at once, the device is erroneously controlled, which sometimes can have very negative effects on the course of the operation.

It is the objective of the present invention to develop a surgical device of the kind cited at the outset further, in such a way that switching between and executing a plurality of modes for controlling the surgical device is ensured, by simple and reliable means.

SUMMARY OF THE INVENTION

In particular the objective is achieved by a surgical apparatus comprising an electrical instrument, in particular for cutting and/or coagulating biological tissue, in which there are disposed on a preferably oblong handle an actuation unit and a control unit, and which makes available at least three modes for controlling the electrical instrument, such that the modes can be selected and hence executed by means of the actuation unit, characterized in that the actuation unit includes a switching rocker with an oblong operating element, which is mounted within a guide device so as to be rotatable about a rocker axis that can be shifted perpendicular to the surface of the handle, in such a way that from an initial position a first or second function position can be reached by forward or backward rotation about the rocker axis and a third function position can be reached by pressing the operating element inward, a sensor being situated on the operating element to the left of the rocker axis and another to its right, so that by means of the sensors the function position selected by the switching rocker can be detected by a control unit. On the handle of the electrical instrument, therefore, there is a rocker switch with which the instrument can be indirectly controlled. For this control various modes are provided by the control unit, and these can be selected and executed by means of the switching rocker.

One advantage of the invention thus resides in the fact that while the surgical apparatus is in use, there is no need to reach around the instrument or even to set it down. This increases the ease of operation of the apparatus, largely excludes the possibility that it will be erroneously controlled because the wrong key has been actuated, and improves both quality and efficiency of the surgical procedure, because the individual modes are rapidly accessible.

It is advantageous for the surgical apparatus that the control unit be designed so that the setting of at least one function position is delayed by a prespecified latency. This means that there is at least one function position that does not elicit an immediate response when detected by the control unit. That is, the control unit delays either the performance of a mode by the electrical instrument, or the change of mode itself. Thus, the physician himself has the opportunity independently to detect a defective operation of the switching rocker and to react to it soon enough to avoid erroneous controlling of the apparatus. With regard to the mechanics, this delay by the prespecified latency has still another advantage. Often mechanically triggered sensors trigger with some delay. Hence it can be the case that with the switching rocker a function position is adopted that one or both sensors do not immediately detect. If this should happen, the function position can be falsely detected by the control unit. A latency adapted to this delay when detecting the function position ensures that the correct function position will be detected.

Preferably, the guide device is designed so that a direct change between the function positions is prevented. Accordingly, there is a mechanical protection against the change from one function position to another. The change between the function positions can be selected from the initial position, only. Such a clear sequence of events prevents the occupation of "intermediate positions" (for instance, a position between the first and third function positions) and ensures an unambiguous and reliable operation of the surgical apparatus. Especially in connection with this mechanical protection, it is helpful for the control unit to be designed such that it enters an error state, in order to signal and/or to eliminate an error, when it is detected that a direct change from one function position into another has been carried out. Since the direct change is not possible on account of the mechanical protection described above, the control unit can diagnose an error in the mechanics or sensors of the actuation device and inform or warn the user of the surgical apparatus accordingly. It is advantageous for the electrical instrument to be put into a secure state when the apparatus has entered this error state.

Preferably the sensors each comprise a key button. These two key buttons can be disposed so that in the first function position only the circuit involving the first button, in the second position only the circuit involving the second button, and in the third position both circuits are closed. This quite simple construction is robust and nevertheless enables the three function positions to be detected.

Preferably there is fixedly connected to the oblong operating element an oblong projection that extends into the handle substantially perpendicular to the rocker axis and to a long axis of the operating element, and that interacts functionally with a guide opening of the guide device in such a way that the operating element can be either rotated or pressed inward. The projection and the oblong operating element form a T-shaped body, the horizontal part of which corresponds to the operating element and the vertical part, to the projection. Starting from the initial state, it is possible to rotate about the rocker axis, which is positioned perpendicular to the horizontal and vertical parts of the T-shaped body. However, if no vertical force is acting on the T-shaped body, at least part of the projection extends into the guide opening and prevents rotation about the rocker axis. Owing to this arrangement, a direct change between the function positions can be prevented, which results in the advantages described above.

Preferably the switching rocker is disposed at the handle in such a way that it is possible simultaneously to operate the switching rocker and to guide the instrument with one hand. A comfortable as well as reliable handling of the instrument is thus guaranteed.

Preferably the control unit is designed such that in one of the function positions, in particular in the first one, at least one mode can be used for cutting biological tissue. As a result, firstly, consistent allocation of a cutting mode to one function position ensures rapid access to this cutting mode while, secondly, errors ascribable to operation of the instrument are avoided.

In addition it is advantageous for the control unit to be designed so that in one of the function positions, in particular in the second one, at least one mode can be used for coagulation of biological tissue. Again, this consistent allocation to a particular function position provides rapid access and reliability in operation.

It has proved advantageous that in the case of a surgical device that makes available two main modes, e.g. cutting and coagulation, as well as for each main mode several subordinate modes, e.g. cutting of liver tissue or cutting of muscle tissue, each of two function positions serves for performance of one of the two main modes, while the third function position can be used to switch between the subordinate modes.

Preferably the switching rocker comprises at least one spring element, disposed below the operating element in such a way that the operating element returns automatically from at least one function position into the initial position. Such a mechanism has proved in practice to be especially operator-friendly and reliable.

BRIEF DESCRIPTION OF THE DRAWINGS

Additional details, advantages and further developments of the invention will be evident from the following description of an exemplary embodiment with reference to the drawings.

DETAILED DESCRIPTION OF THE INVENTION

Figure 1:
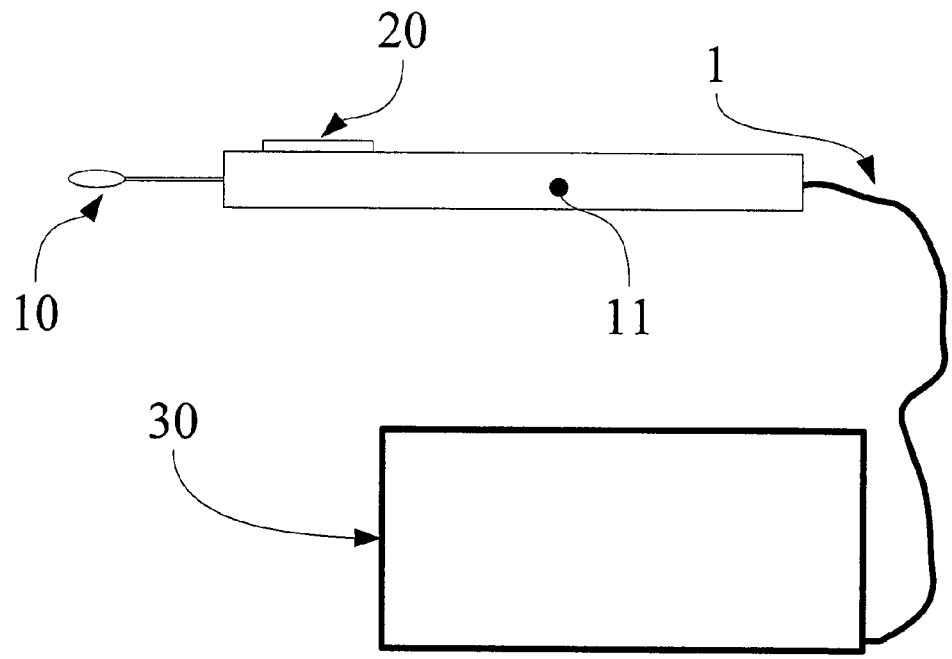
FIG. 1 is a schematic representation of individual components of a surgical apparatus.

In the following description, the same reference numerals are used for identical parts or parts with identical actions.

FIG. 1 shows the most important components of a surgical apparatus. Two main components represented here comprise an instrument 10 with handle 11 and a control unit 30 for controlling the instrument. The two main components are connected to one another by a connecting lead 1. The handle 11 further comprises a switch 20, which is interrogated by the control unit 30 and contributes indirectly to the control of the instrument 10. The control unit 30 has several operating modes, for example a mode for cutting liver tissue and muscle fibres as well as a mode for coagulation. By means of the switch 20 these modes can be selected and executed. The control unit 30 controls the instrument in accordance with the mode that is selected.

Figure 2A:
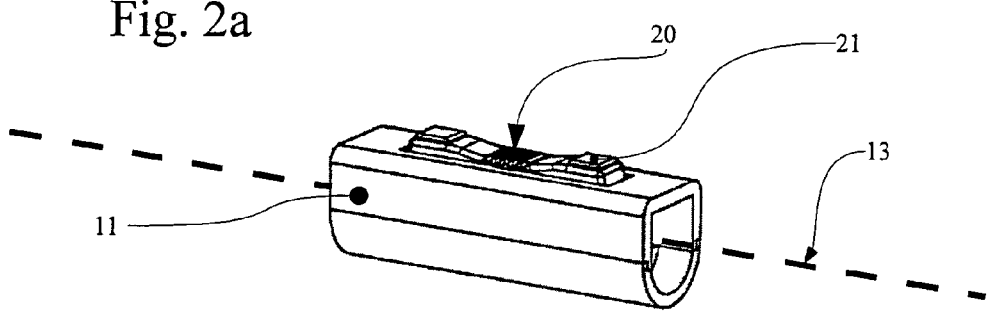
FIGS. 2a to 2c show the construction of a switching rocker.
Figure 2B:
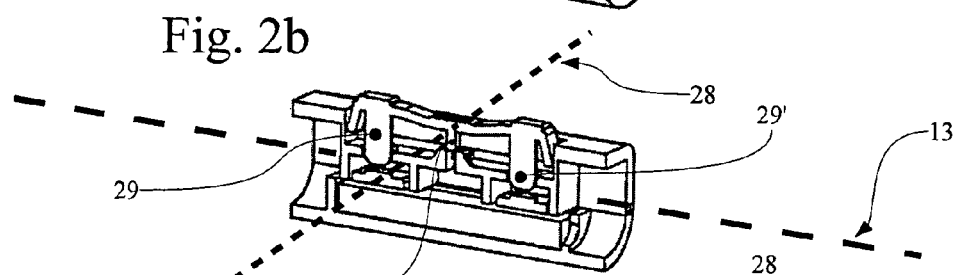
Figure 2C:
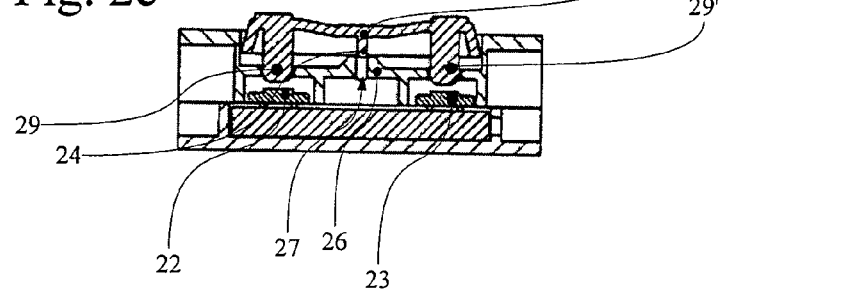

FIG. 2a shows a switch 20, which is integrated into a handle 11. The oblong operating element 21 of the switch 20 is oriented parallel to a handle axis 13. FIG. 2b shows in perspective a cross section through the switch 20 shown in FIG. 2a, along the handle axis 13. A rocker axis 28 has its axis oriented parallel to the surface of the operating element 21, at right angles to the handle axis 13. Two contact elements 29, 29' are symmetrically disposed, one at each end of the operating element 21 on the left and right sides of the rocker axis 28, and project into the interior of the switch 20. FIG. 2c shows a functional cross section through the switch 20 already shown in FIGS. 2a and 2b. The switch 20 comprises the operating element 21 with the contact elements 29, 29' projecting into the interior of the switch. The operating element 21 is held by a guide device 26 in such a way that when a rotational movement about the rocker axis 28 occurs, the contact elements 29, 29' come into contact with sensors 22, 23. If the operating element 21 is pressed inward, perpendicular to the rocker axis 28 and to the handle axis 13, then the projection 24 disposed below the operating element 21 enters a guide opening 27 and from this moment on prevents rotation about the rocker axis 28. If the operating element 21 has been pressed in far enough, both contact elements 29, 29' come into contact with the sensors 22, 23. This causes activation of the sensors 22, 23, which are in communication with the control unit 30 (cf. FIG. 1).

Underneath the operating element 21 spring elements can be provided in a way, so that the operating element 21 returns automatically from any function position back into the initial position as soon as no further force is applied to the operating element 21. A helical spring can for example be positioned around the projection 24. As soon as the operating element 21 is pressed inward, perpendicular to the axis 13 and 28 the helical spring compresses and returns the operating element 21 to its original position as soon as no further pressure is applied.

The sensors 22, 23 shown in the FIG. 2c can be simple electrical switches closing a circuit as soon as one of the contact elements 29, 29' comes in contact with them. The control unit 30 can thus determine the position of the operating element 21. In an alternative embodiment, the sensors 22, 23 might be pressure sensors determining the force applied to one of the sensors 22, 23 through the operating element 21. In this case the control unit 30 might process the amount of pressure applied by a possible user and control the instrument accordingly.

Figure 4A:
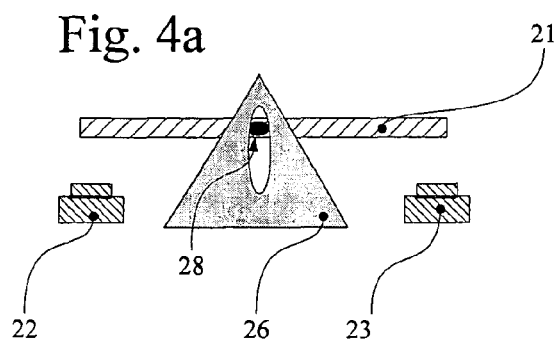
FIGS. 4a to 4d are schematic representations of an initial position, a first, a second and a third function position of a switching rocker.
Figure 4B:
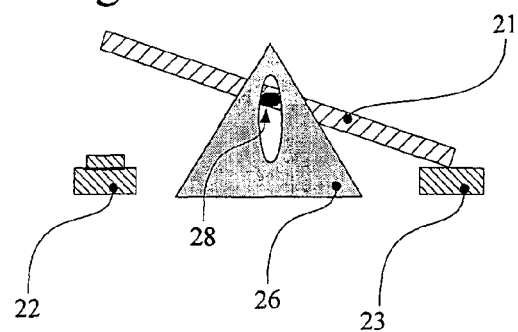
Figure 4C:
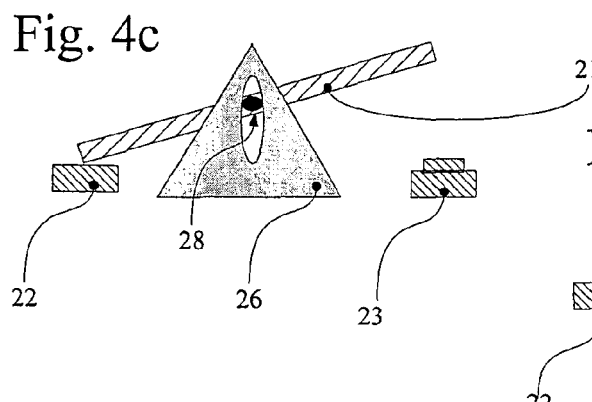
Figure 4D:
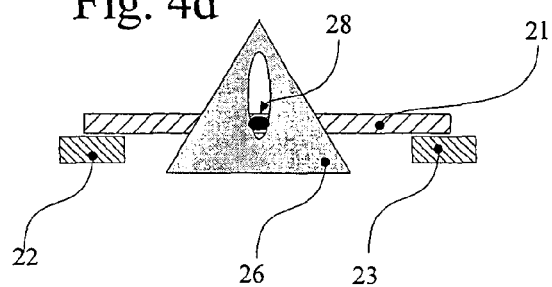

To illustrate the function of the switch 20 shown in FIGS. 2a to 2c, FIGS. 4a to 4d show schematically four possible positions that the operating element 21 can occupy. According to these positions the sensors 22, 23 are triggered, and these, as mentioned above, communicate with the control unit 30 and are used to detect the position of the operating element. Each of the FIGS. 4a to 4d shows schematically the rocker axis 28, the guide device 26, the operating element 21 and the sensors 22, 23 from FIGS. 2a to 2c. In FIG. 4a the operating element 21 is in a horizontal initial position and is not in contact with either the sensor 22 or the sensor 23. In FIG. 4b the operating element 21 has been rotated clockwise about the rocker axis 28 within the guide 26. As a result, the operating element 21 is in contact with the sensor 23. The control unit 30 is thus informed that a first functional position is being occupied. In FIG. 4c the operating element 21 has been rotated counterclockwise about the rocker axis 28. It is now in contact with the sensor 22, so that the control unit 30 can detect a second function position. In FIG. 4d the operating element has been displaced parallel to the initial position, shown in FIG. 4a, towards the sensors 22 and 23. The operating element 21 is now in contact with both sensors 22, 23. Now a third function position of the operating element 21 can be detected by the control unit.

Figure 3:
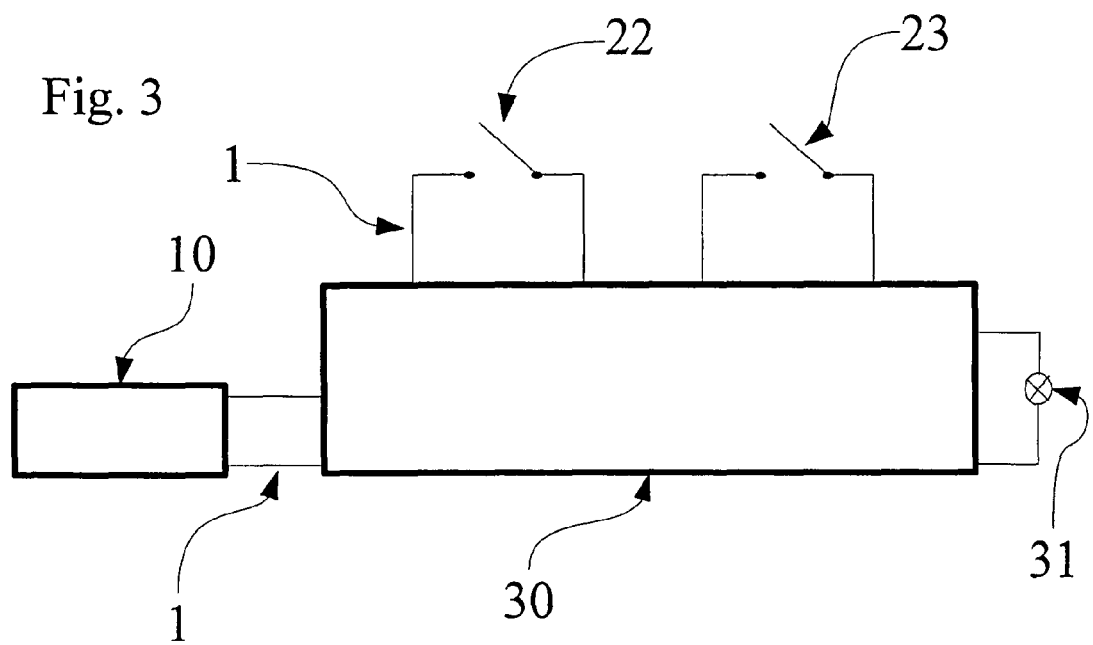
FIG. 3 is a schematic representation of a control unit with corresponding in- and output devices.

A detailed overview of possible inputs and outputs of a control unit 30 corresponding to the control unit 30 in FIG. 1 is given in FIG. 3. The control unit 30 receives inputs from two sensors 22, 23 and controls an instrument 10 by way of a connecting lead 1. The control unit 30 can send out signals to the user of the instrument by way of a warning light 31. Instead of the warning light 31 a vibration alarm, a digital display or the like are also conceivable.

To ensure reliable control of the medical instrument 10 (cf. FIG. 1), the control unit 30 makes a decision on the basis of the signals received from the sensors 22, 23 about the position being occupied by the operating element 21 of the switch 20 and, in a preferred exemplary embodiment after a prespecified latency $t_L$, controls the instrument in accordance with this position. To aid understanding of the logic employed in the control unit 30, FIGS. 5a to 5d show activity diagrams for the control unit 30. In all activity diagrams the time axis runs from top to bottom.

Figure 5A:
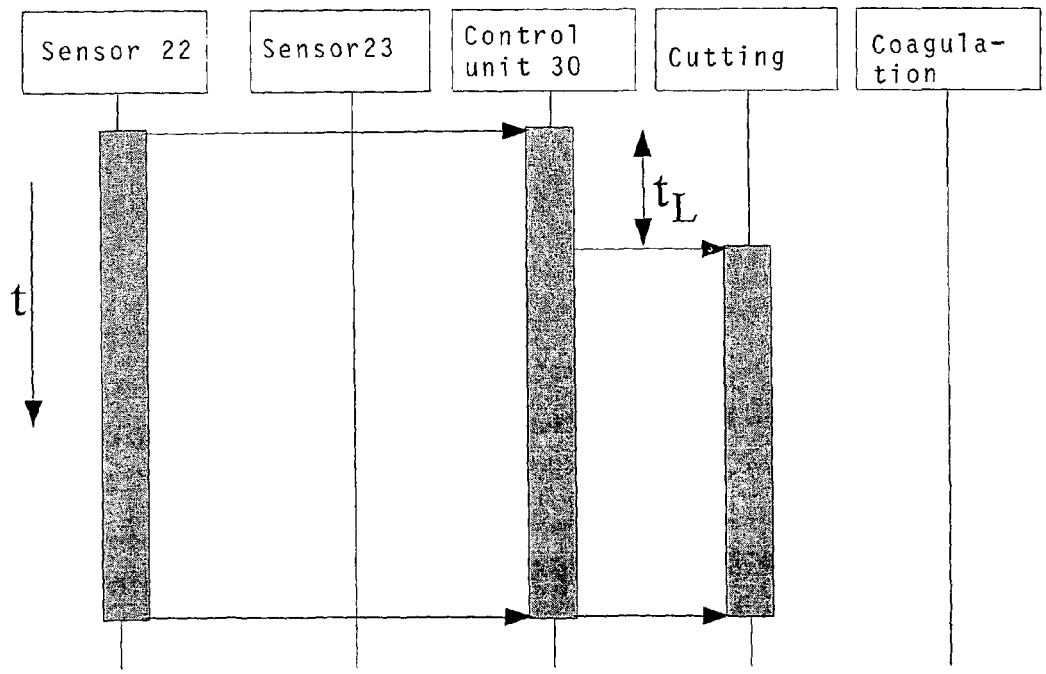
FIG. 5a is an activity diagram for a cutting process.
Figure 5B:
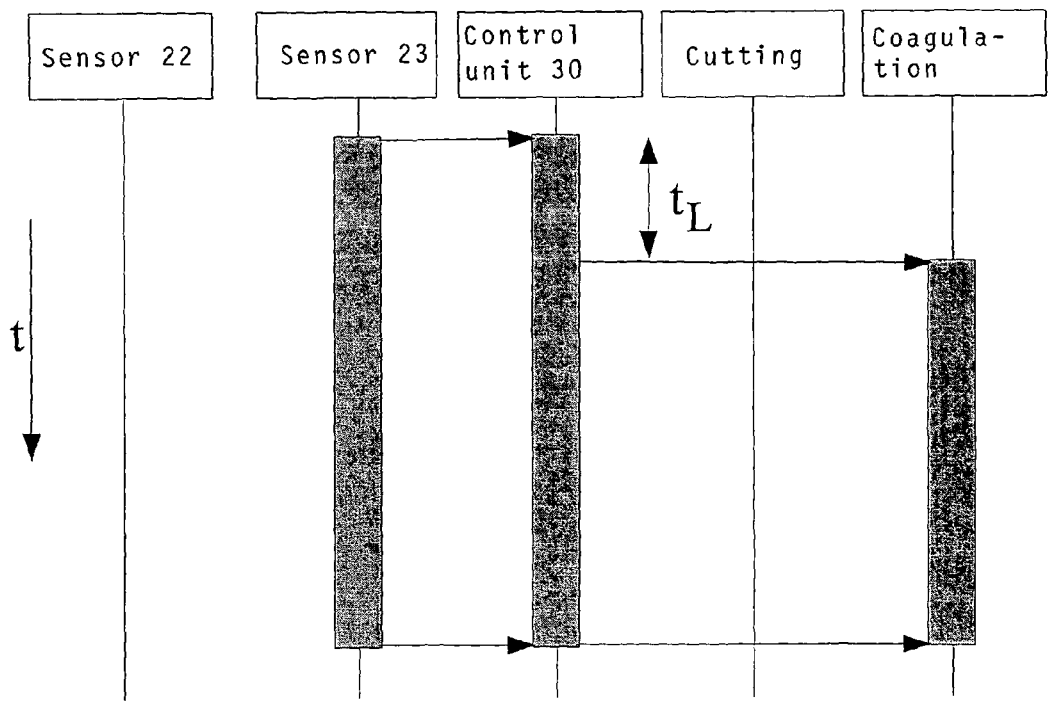
FIG. 5b is an activity diagram for a coagulation process.
Figure 5C:
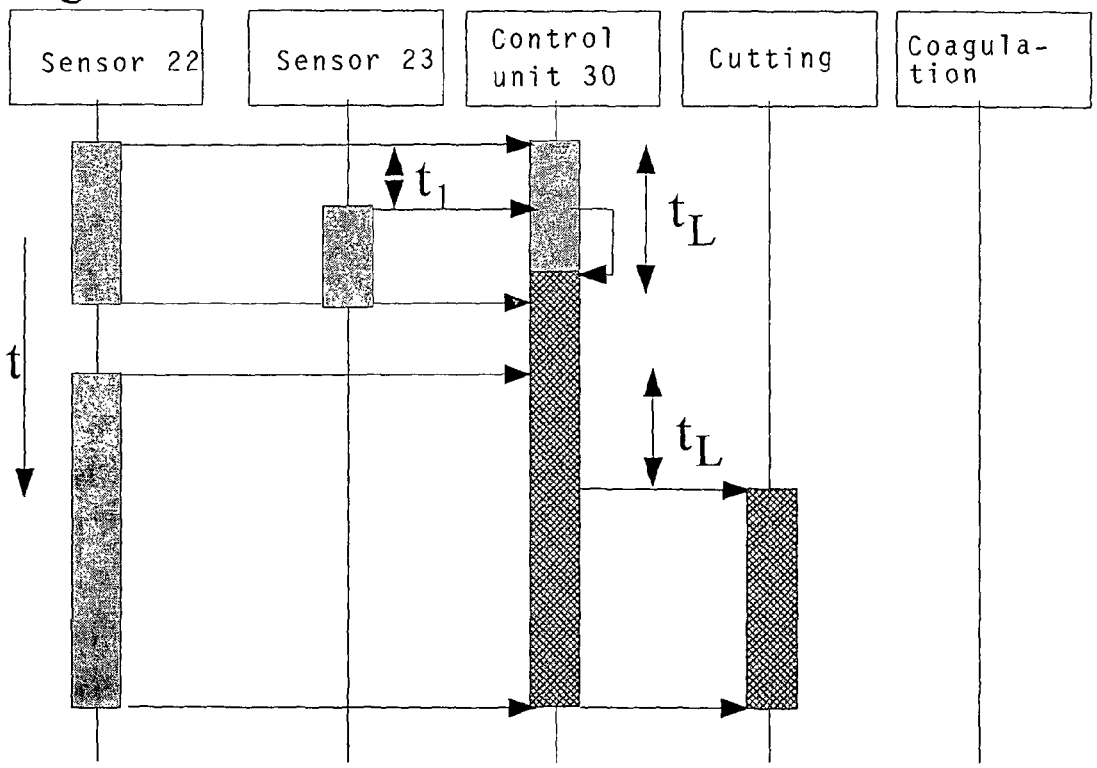
FIG. 5c is an activity diagram for a mode change.

In each of FIGS. 5a to 5c the actors are sensor 22, sensor 23, control unit 30, cutting and coagulation.

FIG. 5a shows how a cutting procedure is carried out. The sensor 22 is activated. The control unit 30 detects this, waits for a prespecified time interval, the so-called latency t, and then causes the cutting procedure to be performed until the control unit 30 determines that the sensor 22 is no longer active.

FIG. 5b shows a coagulation procedure. The sensor 23 is activated and this is detected by the control unit 30. Again the response of the control unit 30 is delayed—by the latency $t_1$. Only then is the coagulation procedure begun. Inactivation of the sensor 23 causes the coagulation procedure to be terminated, by way of the control unit 30.

FIG. 5c shows a change of mode of the control unit 30, followed by a cutting procedure. In this case the control unit 30 detects the consecutive activation of the sensors 22 and 23, separated by a time interval $t_r$. The delay by t, can be caused on one hand by the mechanics of the switch 20, or on the other hand by the sensors 22, 23 themselves. Because the time interval t, is smaller than the latency t, activation of the two sensors 22, 23 results in a change of state of the control unit 30. Specifically this means, in the present example, that the cutting mode is altered. If, as shown below, a new cutting procedure is carried out, this differs from the cutting procedure shown in FIG. 5a. For example, the cutting procedure shown in FIG. 5c can be particularly suitable for cutting muscle tissue, whereas the cutting procedure in FIG. 5a is better adapted to liver tissue. Although in the illustrated example the change of state is effective only for the cutting procedure, by means of a slight change in the logic of the control unit 30 the change of state can be caused from then on, or exclusively, to bring about a change in the coagulation mode.

Figure 5D:
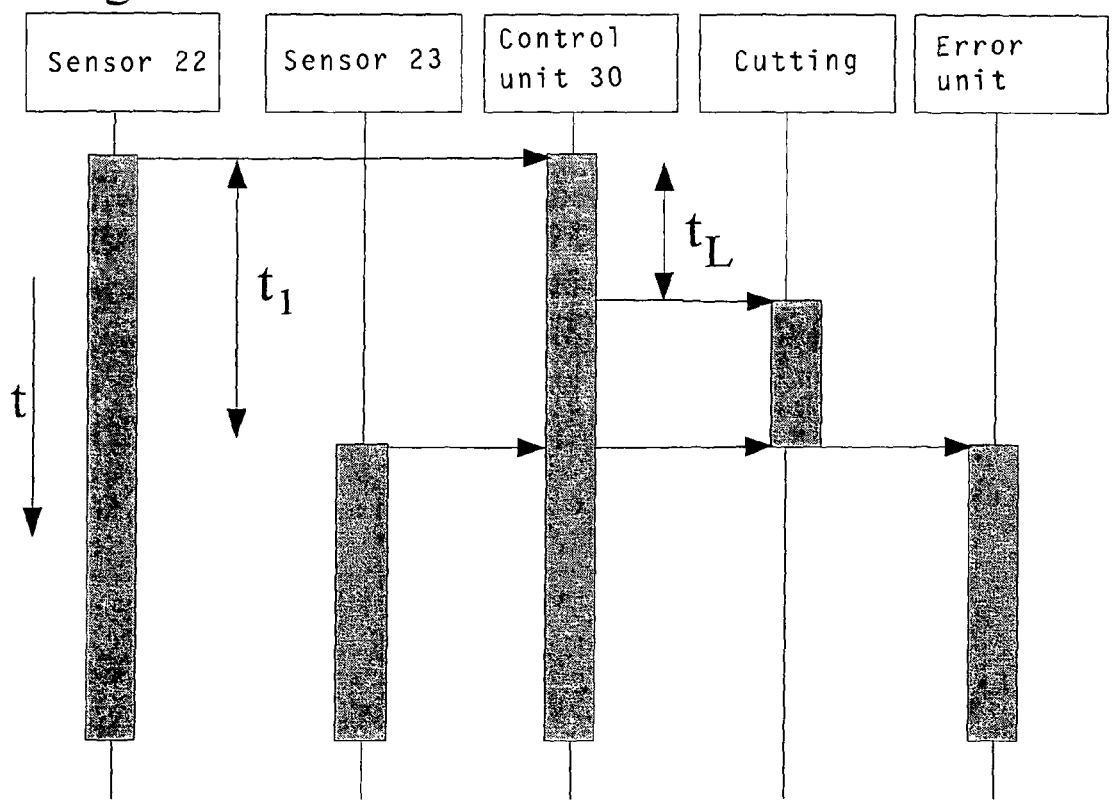
FIG. 5d is an activity diagram for a control unit that results in an error state.

In the activity diagram of FIG. 5d the actors are sensor 22, sensor 23, control unit 30, cutting and error unit. The control unit here detects the activation of the sensor 22, waits until the specified latency $t_L$ has passed, and then causes the cutting procedure to be performed. Delayed by the interval t, from the activation of the sensor 22, the sensor 23 is activated. The control unit 30 detects that the time interval t, is greater than the latency t. Therefore the unit decides that an error has occurred, stops the cutting procedure and activates an error unit. The error unit can, for example, pass on to the user warnings or information about the nature of the error. Because the switch 20 (cf. FIGS. 3a-2c) is designed so that a direct change between the individual function positions is not possible, the control unit 30 can, as shown above, identify malfunctions in the mechanics or at the sensors 22, 23.

LIST OF REFERENCE NUMERALS

1 Connecting lead
10 Instrument
11 Handle
13 Handle axis
20 Switch
21 Operating element
22 Sensor 1
23 Sensor 2
24 Projection
26 Guide device
27 Guide opening
28 Rocker axis
29, 29' Contact element
30 Control unit
31 Warning light

The invention claimed is:
1. A surgical apparatus, comprising:
an instrument that may be used for cutting and/or coagulating biological tissue, with an actuation unit disposed on a handle and a control unit providing at least three modes for controlling the instrument, these modes being selectable and/or executable using the actuation unit,
wherein the actuation unit contains a switching rocker with an oblong operating element mounted in a guide device so as to be rotatable about a rocker axis that can be shifted perpendicular to the surface of the handle, so that starting from an initial position a first or second function position can be reached by forward or backward rotation about the rocker axis and a third function position can be reached by pressing the operating element inward, two sensors being disposed en next to the operating element, one on each of two opposite sides of the rocker axis, in such a way that the function position selected using the switching rocker can be detected by a control unit via the sensors, wherein a guide opening of the guide device is designed to receive a projection in the third function position, the projection being attached to the oblong operating element, and extending into the guide opening in the third function position to prevent a direct change between the function positions.

2. The surgical apparatus according to claim 1,
wherein the control unit is designed such that the detection of at least one function position is delayed by a prespecified time latency.

3. The surgical apparatus according to claim 1,
wherein the control unit is designed so that it enters an error state to signal and/or eliminate an error when the control unit detects that a direct change from one function position into another was carried out.

4. The surgical apparatus according to claim 1,
wherein the sensors each comprise a switch.

5. The surgical apparatus according to claim 1,
wherein the oblong operating element comprises an oblong projection fixedly attached thereto, which projects into the handle substantially perpendicular to the rocker axis and to a longitudinal axis of the operating element, and is functionally connected to a guide opening in the guide device in such a way that the operating element can be either rotated about the rocker axis or pressed inward.

6. The surgical apparatus according to claim 1,
wherein the switching rocker is disposed on the handle in such a way that it is possible simultaneously, with one hand, to operate the switching rocker and to guide the instrument.

7. The surgical apparatus according to claim 1,
wherein the control unit is designed so that in the first function position, at least one mode for the cutting of biological tissue can be performed.

8. The surgical apparatus according to claim 7,
wherein the control unit is designed so that in the third function position, the mode performed via the first function position is altered.

9. The surgical apparatus according to claim 1,
wherein the control unit is designed so that in the second function position, at least one mode for the coagulation of biological tissue can be performed.

10. The surgical apparatus according to claim 9, wherein the control unit is designed so that in the third function position, the mode performed via the second function position is altered.

11. The surgical apparatus according to claim 1,
wherein the switching rocker comprises at least one spring element, which is mounted below the operating element in such a way that the operating element automatically returns from at least one function position into the initial position.

\* \* \* \* \*